(12) United States Patent
McElroy et al.

(10) Patent No.: US 11,179,370 B2
(45) Date of Patent: *Nov. 23, 2021

(54) CANNABINOID RECEPTOR ANTAGONISTS/INVERSE AGONISTS USEFUL FOR TREATING DISEASE CONDITIONS, INCLUDING METABOLIC DISORDERS AND CANCERS

(71) Applicant: Jenrin Discovery, LLC, Chadds Ford, PA (US)

(72) Inventors: John F McElroy, Wilmington, DE (US); Robert J. Chorvat, Chadds Ford, PA (US)

(73) Assignee: Jenrin Discovery, LLC, Chadds Ford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/809,380

(22) Filed: Mar. 4, 2020

(65) Prior Publication Data
US 2021/0023054 A1 Jan. 28, 2021

Related U.S. Application Data

(63) Continuation of application No. 15/991,705, filed on May 29, 2018, now Pat. No. 10,617,673, which is a continuation of application No. 15/377,662, filed on Dec. 13, 2016, now Pat. No. 9,987,253, which is a continuation of application No. 14/844,297, filed on Sep. 3, 2015, now Pat. No. 9,517,228, which is a continuation of application No. 14/191,922, filed on Feb. 27, 2014, now Pat. No. 9,133,127, which is a continuation of application No. 13/950,195, filed on Jul. 24, 2013, now Pat. No. 8,680,131.

(60) Provisional application No. 61/787,214, filed on Mar. 15, 2013, provisional application No. 61/675,806, filed on Jul. 25, 2012.

(51) Int. Cl.
*A61K 31/415* (2006.01)
*C07D 231/06* (2006.01)
*A61K 45/06* (2006.01)

(52) U.S. Cl.
CPC ............ *A61K 31/415* (2013.01); *A61K 45/06* (2013.01); *C07D 231/06* (2013.01)

(58) Field of Classification Search
None
See application file for complete search history.

(56) References Cited

U.S. PATENT DOCUMENTS

| | | |
|---|---|---|
| 6,476,060 B2 | 11/2002 | Lange et al. |
| 6,974,810 B2 | 12/2005 | Lange et al. |
| 7,482,470 B2 | 1/2009 | McElroy et al. |
| 7,528,162 B2 | 5/2009 | Kruse et al. |
| 7,655,685 B2 | 2/2010 | McElroy et al. |
| 7,666,889 B2 | 2/2010 | McElroy et al. |
| 8,088,809 B2 | 1/2012 | McElroy et al. |
| 8,138,216 B2 | 3/2012 | McElroy et al. |
| 8,580,768 B2 | 11/2013 | McElroy et al. |
| 8,680,131 B2 | 3/2014 | McElroy et al. |
| 2008/0255093 A1 | 10/2008 | Tam et al. |
| 2012/0264797 A1 | 10/2012 | McElroy et al. |
| 2013/0005784 A1 | 1/2013 | McElroy et al. |

FOREIGN PATENT DOCUMENTS

| | | |
|---|---|---|
| EP | 1429761 -62 | 11/2006 |
| WO | WO-02/076949 A1 | 10/2002 |

OTHER PUBLICATIONS

U.S. Appl. No. 14/065,376, McElroy et al.
New data shows Acomplia(r) (rimonabant) benefited patients with type 2 diabetes by improving blood sugar control reducing weight and acting on other cardiometabolic risk factors. Cape Town, South Africa, Dec. 5, 2006: http://en.sanofi-aventis.com/press_releases/2006/ppc_15161.asp.
Lange, J.H.M et al., Synthesis, Biological Properties and Molecular Investigations of Novel 3,4-Diarylpyrazolines as Potent and Selective CB1 Cannabinoid Receptor Antagonists; J. Med. Chem. 2004, 47, 627-643.
Remington, et al. The Science and Practice of Pharmacy, 2000, Lippincott Williams and Wilkins, 20th Edition, pp. 218-220.
Wierzbicki, A.S., Rimonabant: endocannabinoid inhibition for the metabolic syndrome, Drug Focus 2006, 60(12), 1697-1706.
Pi-Sunyer, F.X., Effect of Rimonabant, a Cannabinoid-1 Receptor Blocker, on Weight and Cardiometabolic Risk Factors in Overweight or Obese Patients, JAMA 2006, 297(7), 761-775.
Solvay's SLV319 Obesity Candidate Treatment Advances in Phase II Clinical Trials, Solvay Press Release, Dec. 8, 2006.
STRADIVARIUS (Strategy to Reduce Althersclerosis Development Involving Administration of Rimonabant-t—the Intravascular Ultrasound Study), Clinical Trials.gov, http://clinicaltrials.gov/ct2/show/study/NCT00124332, Jul. 26, 2005.
Tam, Joseph et al., Peripheral CB1 Cannabinoid Receptor Blockade Imiproves Cardiometabolic Risk in Mouse models of Obesity. Journal of Clinical Investigation 2010, 120(8), 2953-2966.

(Continued)

*Primary Examiner* — Samantha L Shterengarts
(74) *Attorney, Agent, or Firm* — Clark & Elbing LLP

(57) ABSTRACT

The present invention provides novel, diastereomeric pyrazolines that are useful as cannabinoid receptor blockers and pharmaceutical compositions thereof and methods of using the same for treating obesity, diabetes, inflammatory disorders, cardiometabolic disorders, hepatic disorders, and/or cancers.

20 Claims, No Drawings

(56) References Cited

OTHER PUBLICATIONS

Kapur, et al., Mutation Studies of Ser7.39 and Ser2.60 in the Human CB1 Cannabinoid Receptor: Evidence for a Serine-Induced Bend in CB1 Transmembrane Helix 7, Mol. Pharmacol. 2007, 71, 1512-24.
PCT/US13/51919 International Search Report and Written Opinion, dated Dec. 30, 2013.
CN Application No. 20138004876569 Office Action Report dated Mar. 13, 2017 (corresponding Chinese application).

CANNABINOID RECEPTOR ANTAGONISTS/INVERSE AGONISTS USEFUL FOR TREATING DISEASE CONDITIONS, INCLUDING METABOLIC DISORDERS AND CANCERS

FIELD OF THE INVENTION

The present invention provides pyrazoline cannabinoid receptor antagonists/inverse agonists and pharmaceutical compositions thereof and methods of using the same for treating disease conditions including inflammatory diseases, metabolic diseases such as obesity, diabetes, and hepatic disorders, cardiometabolic disorders, and cancers.

BACKGROUND OF THE INVENTION

The endocannabinoid system (ECS) is comprised of two cannabinoid receptor subtypes (CB1 and CB2), their endogenous ligands (i.e., the endocannabinoids anandamide and 2-arachidonoyl glycerol), and enzymes for ligand biosynthesis and degradation (e.g., monoacylglycerol lipase, fatty acid amide hydrolase). The ECS plays a prominent role in the regulation of a variety of physiological functions, including control of food intake and energy metabolism, emotional behavior, pain, cell division, and inflammation. CB1 receptors are widely expressed in numerous peripheral organs and tissues, including thyroid gland, adrenal gland, reproductive organs, bone, adipose tissue, liver, muscle, pancreas, kidney, and gastrointestinal tract. CB1 receptors have also been identified in brain, including cortex, hippocampus, amygdala, pituitary and hypothalamus. CB2 receptors are largely localized in immune and blood cells, but have more recently been identified in brain [for reviews see *Endocrine Reviews* 2006, 27, 73; *Int J Obesity* 2006, 30, S30; *J Clin Endocrin Metab* 2006, 91, 3171; *Int J Obesity* 2009, 33, 947].

Many disease states, including inflammatory and metabolic diseases and certain cancers are associated with overactivity of the ECS system. This is characterized by increased ECS tone in peripheral tissues including adipose, liver, muscle, and pancreas. Elevated ECS tone is reflected by increased tissue expression of CB1 receptors as well as elevated tissue levels of the main endogenous cannabinoids anandamide and/or 2-arachidonoyl glycerol. Preventing and/or reversing overactivity of the ECS system has proven to be a useful approach toward the treatment of inflammatory and metabolic diseases and certain cancers [*Mol Pharmacol* 2003,63, 908; *J Clin Invest* 2008; 118:3160; *Diabetes* 2010, 59, 926; *Cancer Res* 2011, 71, 7471; *Cell Metab* 2010; 11:273; *J Biol Chem* 2008; 283:33021; *Int J Obesity* 2007, 31, 692].

The plant-derived cannabinoid agonist $\Delta^9$-tetrahydrocannabinol ($\Delta^9$-THC), the main psychoactive component of marijuana, binds to both CB1 and CB2 receptors. $\Delta^9$-THC is widely reported to increase appetite and food intake (hyperphagia) in humans and in animals. This hyperphagic effect is largely blocked by pretreatment with CB1 antagonists and inverse agonists (e.g., rimonabant, taranabant, otenabant, ibipinabant), drugs that effectively block the CB1 receptor, strongly supporting the belief that CB1 receptor activation mediates the hyperphagic effect of $\Delta^9$-THC, [*Endocrine Reviews* 2006, 27, 73].

In humans, rimonabant and taranabant produce a clinically meaningful weight loss in obese patients. Obese patients also experience improvements in diabetic and cardiometabolic risk factors associated with obesity, including an increase in the level of high density lipoprotein cholesterol (HDL), and decreases in triglycerides, glucose, and hemoglobin A1c (HbA1c, a marker of cumulative exposure to glucose) levels. Rimonabant also produces reductions in abdominal fat deposits, which are a known risk factor for diabetes and heart disease [*Science* 2006, 311, 323]. Taken together, these improvements in adiposity and cardiometabolic risk factors produce an overall decrease in the prevalence of the metabolic syndrome [*Lancet* 2005, 365, 1389 and *NEJM* 2005, 353, 2121].

In patients with type 2 diabetes not currently treated with other anti-diabetic medications, rimonabant was shown to significantly improve blood sugar control and weight, as well as other risk factors such as HDL and triglycerides, when compared to placebo. After six months of treatment, HbA1c levels were significantly lowered by 0.8% from a baseline value of 7.9 as compared to a reduction of 0.3% in the placebo group [(*Diabetes Care* 2008, 31, 2169; *Lancet* 2006, 368(9548), 1660-7]. Rimonabant also improved glycemic control and cardiometabolic risk factors in type 2 diabetic patients receiving insulin [*Diabetes Care* 2010, 33, 605]. These results are consistent with preclinical studies that demonstrate improved glycemic and lipid control in diabetic and dyslipidemic mice, rats, and dogs (*Pharmacology Biochemistry & Behavior,* 2006, 84, 353; *American Journal of Physiology,* 2003, 284, R345; *American Diabetes Association Annual Meeting,* 2007; Abstract Number 0372-OR).

The beneficial effects of rimonabant on diabetic and cardiometabolic risk factors such as high blood pressure, insulin resistance, and elevated triglycerides cannot be explained by diet-related weight loss alone. For example, in patients receiving 20 mg of rimonabant, only approximately 50% of the beneficial effects on triglycerides, fasting insulin, and insulin resistance can be accounted for by weight loss secondary to reduced food intake. These results suggest a direct pharmacological effect of CB1 antagonists on glucose and lipid metabolism, in addition to indirect effects on metabolism secondary to hypophagia-mediated weight loss [*Science* 2006, 311, 323 and *JAMA* 2006, 311, 323]. Taken together, these results suggest that CB1 antagonists might be effective in the treatment of diabetes, dyslipidemias (e.g., high triglycerides and LDL, low HDL), cardiovascular disorders (e.g., atherosclerosis, hypertension), and hepatic disorders (e.g., fatty liver diseases, non-alcoholic steatohepatitis, cirrhosis, liver cancers), even in patients that are not clinically overweight or obese.

The CB1 receptor is overexpressed in alveolar rhabdomyosarcoma (ARMS), a pediatric soft tissue tumor derived from skeletal muscle, and upregulation of CB1 is a diagnostic marker for ARMS [*Cancer Res* 2004, 64, 5539]. CB1 overexpression is essential for tumor cell proliferation and metastasis, and the CB1 inverse agonist AM251 abrogates both cell invasion and lung metastasis in vivo [*Cancer Res* 2011, 71, 7471]. The CB1 inverse agonist rimonabant has also been demonstrated to inhibit human breast and prostate cancer proliferation [*Mol Pharmacol* 2006, 70, 1298; *Cancer Res* 2005, 65, 1635], and to inhibit human colon cancer cell growth and reduce the formation of precancerous lesions in the mouse colon [*Int J Cancer* 2009, 125, 996].

The CB1 receptor is one of the most abundant and widely distributed G protein-coupled receptors in the mammalian brain. It is now known that the appetite-suppressant properties of CB1 antagonists can be mediated through either a direct action with CB1 receptors in brain regions associated with hunger and satiety (e.g., hypothalamus, mesolimbic regions), or a direct action with CB1 receptors in peripheral tissues (e.g., adipose tissue, kidney) [*J. Clin Invest* 2010, 120: 2953; *Obesity* 2011, 19: 1325] However, CB1 receptors are far more broadly distributed in brain (e.g., neocortex, hippocampus, thalamus, cerebellum, and pituitary), and while interacting with targeted CB1 receptors in hypothalamus and mesolimbic regions to suppress appetite, CB1 antagonists have equal access to non-targeted CB1 receptors that have little if any role in appetite control. Binding to non-targeted receptors can often lead to unwanted side effects of CNS drugs [*Endocrine Reviews* 2006, 27:73]. The CB1 blockers rimonabant and taranabant produce psychiatric and neurological side effects. These include depressed mood, anxiety, irritability, insomnia, dizziness, headache, seizures, and suicidality.

These side effects are dose-related and appear pronounced at the most efficacious weight-reducing doses of rimonabant and taranabant (*JAMA* 2006, 311, 323; *Cell Metabolism* 2008, 7, 68). The occurrence of therapeutic efficacy (appetite suppression) and side effects over the same dose range strongly suggest that both effects are mediated through concurrent blockade of CB1 receptors in both 'targeted' and 'non-targeted' brain regions. Brain-penetrant CB1 blockers do not selectively target CB1 receptors in efficacy brain regions, while ignoring CB1 receptors in side effect brain regions.

The beneficial effects of the CB1 antagonist rimonabant on body weight, adiposity, and diabetic and cardiometabolic risk factors such as high blood pressure, insulin resistance and blood lipids cannot be explained by weight loss derived from CNS-mediated appetite suppression alone [*JAMA* 2006, 311, 323]. At least 50% of the benefit is likely derived from an interaction with CB1 receptors in peripheral tissues known to play an active role in metabolism. These include adipose tissue, liver, muscle, pancreas, kidney, reproductive tissues, and gastrointestinal tract.

In view of the above, it is highly desirable to find effective and highly selective CB1 receptor blockers with limited or no CNS adverse side effects, including mood disorders. Particularly, it is desirable to find compounds that preferentially target CB1 receptors in peripheral tissues (e.g., adipose tissue, liver, muscle, pancreas, reproductive tissues and gastrointestinal tract), while sparing CB1 receptors in brain. In this way, peripherally-mediated beneficial effects of CB1 blockers can be maintained, whereas CNS side effects will be reduced or eliminated. This should provide a novel opportunity to develop safer alternatives to highly brain penetrant CB1 blockers for the prevention or treatment of obesity, diabetes, dyslipidemia, cardiovascular disorders, hepatic disorders, and/or certain cancers.

SUMMARY OF THE INVENTION

Accordingly, in an aspect, the present invention provides novel pyrazolines or pharmaceutically acceptable salts thereof that are CB1 receptor antagonists/inverse agonists.

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating obesity, diabetes (e.g., insulin resistance, inadequate glucose tolerance, Type I diabetes, and Type II diabetes), dyslipidemias (e.g., elevated triglycerides and LDL, and low HDL), cardiovascular disorders (e.g., atherosclerosis and hypertension), inflammatory disorders (e.g., osteoarthritis, rheumatoid arthritis, inflammatory bowel diseases, and obesity-associated inflammation), hepatic disorders (e.g., nonalcoholic and alcoholic steatohepatitis, cirrhosis and fatty liver disease), and/or cancer (e.g., colon, breast, thyroid, and alveolar rhabdomyosarcoma cancer), comprising: administering to a mammal in need of such treatment a therapeutically effective amount of at least one of the compounds of the present invention or a pharmaceutically acceptable salt form thereof.

In another aspect, the present invention provides processes for preparing novel compounds.

In another aspect, the present invention provides novel compounds or pharmaceutically acceptable salts for use in therapy.

In another aspect, the present invention provides the use of novel compounds for the manufacture of a medicament for the treatment of obesity, diabetes, dyslipidemia, cardiovascular disorders, hepatic disorders, and/or certain cancers.

These and other objects, which will become apparent during the following detailed description, have been achieved by the inventors' discovery that the presently claimed compounds or pharmaceutically acceptable salt forms thereof are expected to be effective CB1 receptor blockers.

DETAILED DESCRIPTION OF THE INVENTION

All references cited herein are hereby incorporated in their entirety herein by reference.

A CB1 blocker is a neutral CB1 receptor antagonist and/or a CB1 receptor inverse agonist.

The present invention is based on the finding that a CB1 receptor blocker has beneficial effects on metabolic disorders including obesity, diabetes, dyslipidemias, and liver diseases that cannot be explained by weight loss derived from CNS-mediated appetite suppression alone, and that this effect is mediated, at least in part, through interaction at peripheral CB1 receptors. To this end, the present invention provides compounds that are designed to preferentially target CB1 receptors in peripheral tissues (e.g., adipose tissue, liver, muscle, pancreas, kidney, and gastrointestinal tract), while sparing CB1 receptors in brain. With these types of compounds, peripherally-mediated beneficial effects of CB1 blockers should be maintained, whereas CNS side effects should be reduced or eliminated.

The compounds of the present invention have been designed to have reduced CNS exposure by virtue of their inability or limited ability to penetrate the blood-brain barrier (BBB), or by their participation in active transport systems, thus reducing centrally mediated side-effects, a potential problem with many anti-obesity agents. It is expected that the peripherally restricted compounds of the present invention will have no or very limited CNS effects, including mood disorders, seizures, and suicidality. Thus, their peripherally mediated CB1 antagonistic properties should provide therapeutic agents with greater safety.

Moreover, if the maximum dosage of a CB1 antagonist/inverse agonist used in the treatment of obesity, diabetes, dyslipidemia, cardiovascular disorders, inflammatory disorders, hepatic disorders, and/or cancers is limited as a result of CNS side effects (e.g., seizures, depression, anxiety, suicidality, movement disorders, and hyperactivity), incorporation of a peripherally restricting group in such a drug would lower the brain concentration of the drug relative to the concentration in the systemic circulation, thereby affording the opportunity to increase the dosage employed to treat the peripheral disorder (e.g., obesity, diabetes, dyslipidemia, cardiovascular disorders, inflammatory disorders, hepatic disorders, and/or cancers). The increased dosage may provide greater therapeutic efficacy, as well as a more rapid onset of therapeutic action.

In an aspect, the present invention provides novel compound selected from Examples 1-4, all of which having chiral centers were prepared from natural (L) forms of amino acids:

1

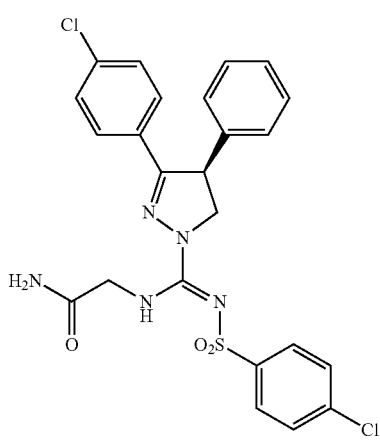

2

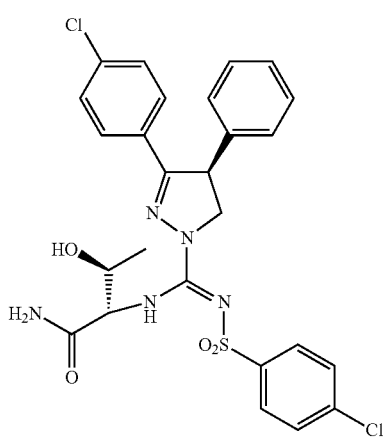

3

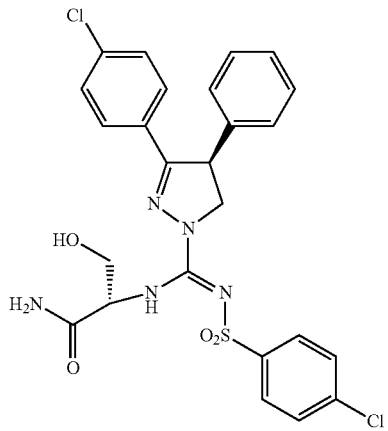

4

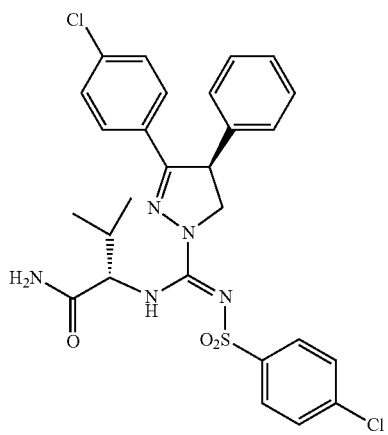

or a pharmaceutically acceptable salt thereof.

In another aspect, the stereometric purity of a desired stereoisomer (e.g., an enantiomer of compound 1 or a single diastereomer of compounds 2-4) is selected from at least 60% to about 99.8%, additional examples include 60, 65, 70, 75, 80, 85, 90, 95, 99, 99.1, 99.2, 99.3, 99.4, 99.5, 99.6, 99.7, to about 99.8%.

In another aspect, the present invention provides deuterium enriched compounds. In these compounds, one or more of the hydrogen atoms are replaced by deuterium. This type of deuterium incorporation or enrichment can be achieved through the use of deuterated starting materials (e.g., L-threonine-2,3-$d_2$) or through deuterium exchange in NaOD/$D_2O$ if the hydrogen of the final product is acidic.

A deuterium-enriched compound is a measurable quantity of molecules wherein the natural abundance of deuterium (0.015%) is raised. Measurable quantity includes at least (a) a mg, (b) 10 mg, (c) 100 mg, (d) a gram, (e) 10 g, (f) 100 g, (g) a kg and up to an appropriate scale for drug manufacturing. Further examples include kilo-lab scale (e.g., 1, 2, 3, 4, 5 kg, etc.) and industrial or commercial scale (e.g., multi-kilogram or above scale including 100, 200, 300, 400, 500 kg, etc.).

Examples A-V of Table A show representative structures of compounds of the present invention wherein deuterated starting materials have been used. The level of deuterium incorporation achieved is dependent about the purity of the starting material as well as reaction conditions if the deuterium is acid. Examples of incorporation levels include 30, 40, 50, 60, 70, 80, 90, 91, 92, 93, 94, 95, 96, 97, 98, 99, to about 100%.

TABLE A
| Ex. # | Deuterium-Enriched Compounds | Deuterated Starting Material |
|---|---|---|
| A. | 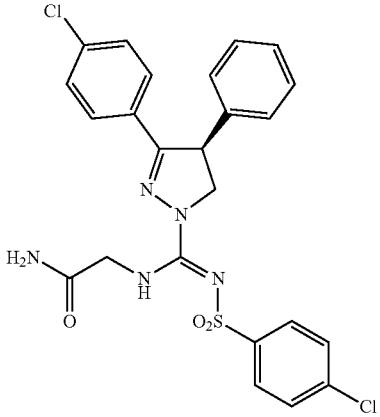 [SMILES: NC(=O)CN/C(=N\S(=O)(=O)c1ccc(Cl)cc1)N1C[C@H](c2ccccc2)C(c2ccc(Cl)cc2)=N1]<br>Glycine's 2-position CH₂ moiety is CD₂<br>(2 deuteriums) | $H_2NC(D_2)C(O)NH_2$ |
| B. | 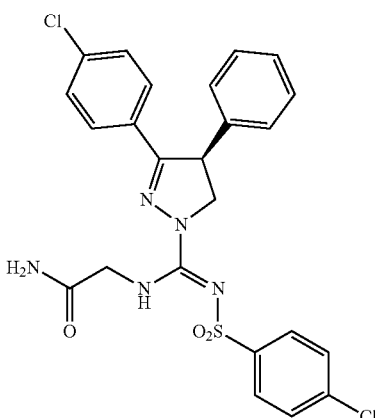<br>Glycine's 2-position CH₂ moiety is CD₂<br>(2 deuteriums) | $H_2NC(D_2)C(O)NH_2$ |
| C. | 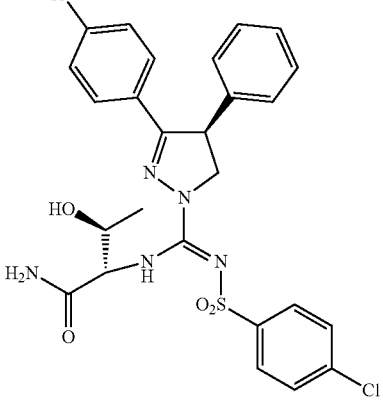<br>Threonine's CHCH moiety is CDCD<br>(2 deuteriums) | L-Threonine-2,3-d₂ |

TABLE A-continued
| Ex. # | Deuterium-Enriched Compounds | Deuterated Starting Material |
|---|---|---|
| D. | 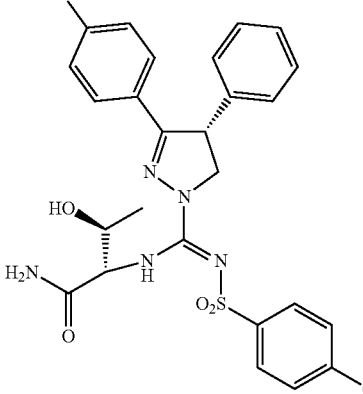 Threonine's CHCH moiety is CDCD (2 deuteriums) | L-Threonine-2,3-d$_2$ |
| E. | 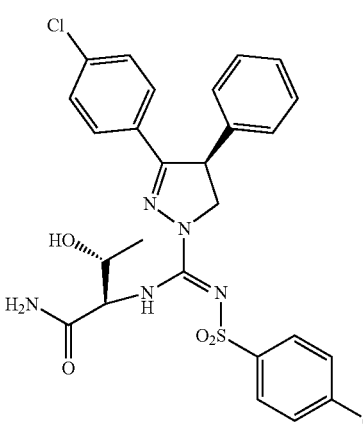 Threonine's CHCH moiety is CDCD (2 deuteriums) | D-Threonine-2,3-d$_2$ |
| F. | 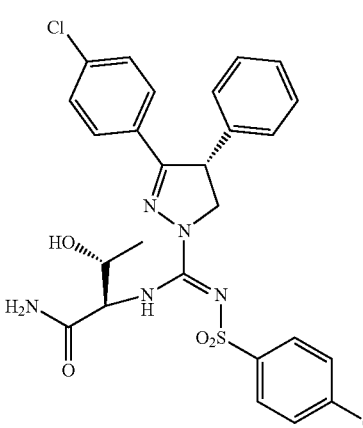 Threonine's CHCH moiety is CDCD (2 deuteriums) | D-Threonine-2,3-d$_2$ |

TABLE A-continued
| Ex. # | Deuterium-Enriched Compounds | Deuterated Starting Material |
|---|---|---|
| G. | 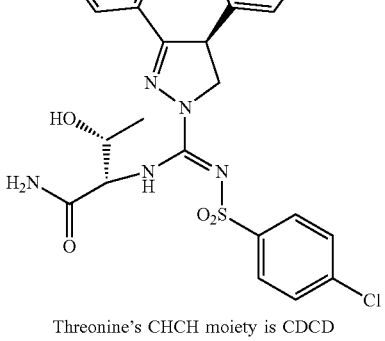 Threonine's CHCH moiety is CDCD (2 deuteriums) | L-Threonine-2,3-$d_2$ |
| H. | 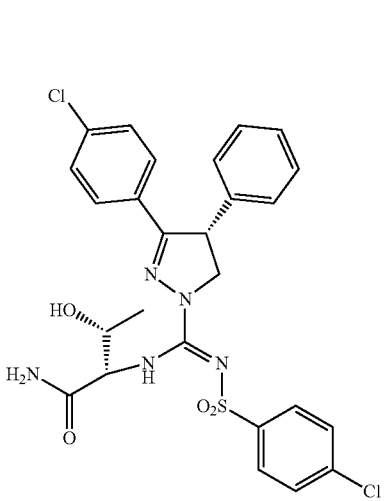 [SMILES: C[C@@H](O)[C@H](N/C(=N\S(=O)(=O)c1ccc(Cl)cc1)N1C[C@@H](c2ccccc2)C(c2ccc(Cl)cc2)=N1)C(N)=O] Threonine's CHCH moiety is CDCD (2 deuteriums) | L-Threonine-2,3-$d_2$ |
| I. | 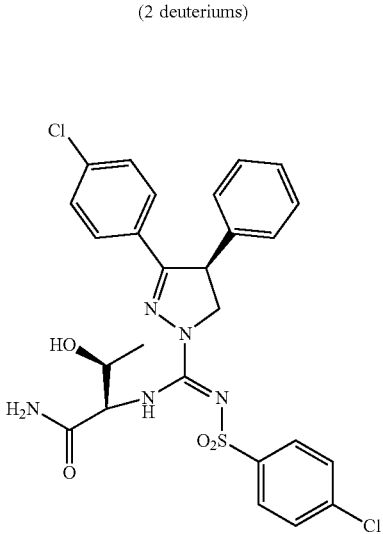 Threonine's CHCH moiety is CDCD (2 deuteriums) | D-Threonine-2,3-$d_2$ |

TABLE A-continued
| Ex. # | Deuterium-Enriched Compounds | Deuterated Starting Material |
|---|---|---|
| J. | 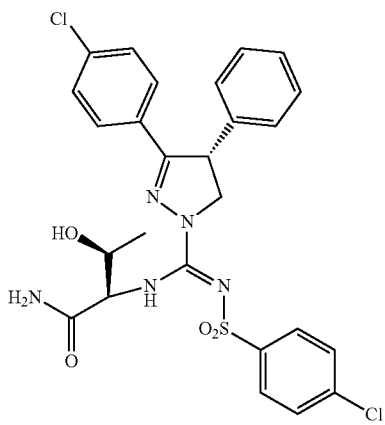 [SMILES: C[C@H](O)[C@@H](N/C(=N\S(=O)(=O)c1ccc(Cl)cc1)N1C[C@@H](c2ccccc2)C(c2ccc(Cl)cc2)=N1)C(N)=O]  Threonine's CHCH moiety is CDCD  (2 deuteriums) | D-Threonine-2,3-$d_2$ |
| K. | 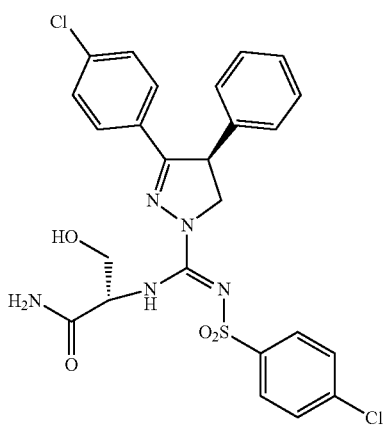 [SMILES: NC(=O)[C@H](CO)N/C(=N\S(=O)(=O)c1ccc(Cl)cc1)N1C[C@H](c2ccccc2)C(c2ccc(Cl)cc2)=N1]  Serine's CHCH$_2$ moiety is CDCD$_2$  (3 deuteriums) | L-Serine-2,3,3-$d_3$ |
| L. | 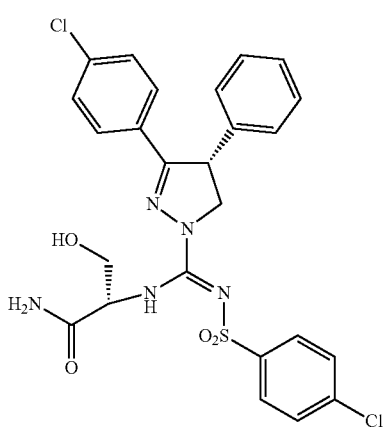 [SMILES: NC(=O)[C@H](CO)N/C(=N\S(=O)(=O)c1ccc(Cl)cc1)N1C[C@@H](c2ccccc2)C(c2ccc(Cl)cc2)=N1]  Serine's CHCH$_2$ moiety is CDCD$_2$  (3 deuteriums) | L-Serine-2,3,3-$d_3$ |

TABLE A-continued
| Ex. # | Deuterium-Enriched Compounds | Deuterated Starting Material |
|---|---|---|
| M. | 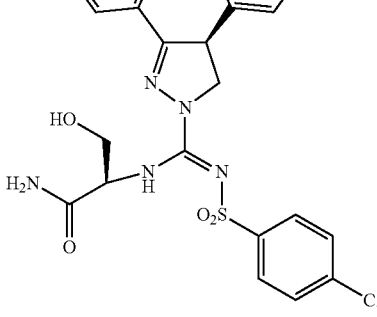<br>Serine's CHCH$_2$ moiety is CDCD$_2$<br>(3 deuteriums) | D-Serine-2,3,3-d$_3$ |
| N. | 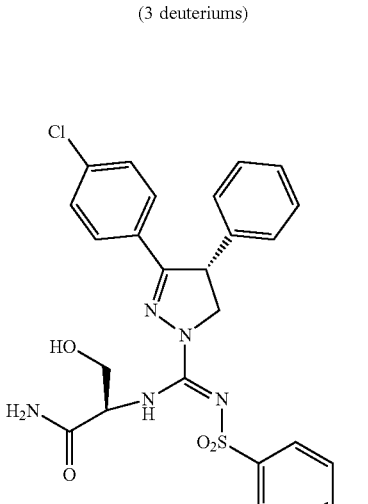<br>Serine's CHCH$_2$ moiety is CDCD$_2$<br>(3 deuteriums) | D-Serine-2,3,3-d$_3$ |
| O. | 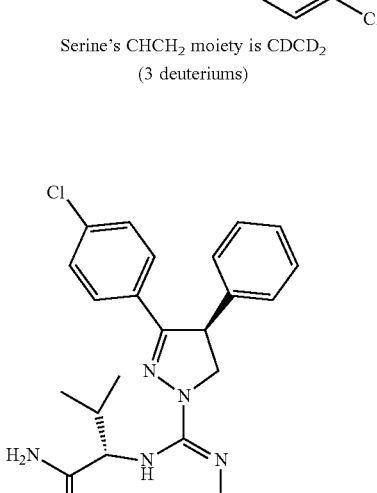<br>Valine's 2-position CH moiety is CD<br>(1 deuterium) | L-Valine-2-d$_1$ |

TABLE A-continued
| Ex. # | Deuterium-Enriched Compounds | Deuterated Starting Material |
|---|---|---|
| P. | 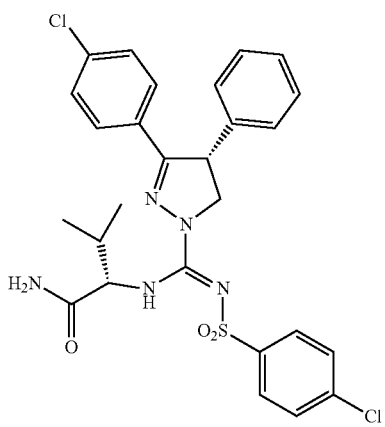 [SMILES: CC(C)[C@H](N/C(=N\S(=O)(=O)c1ccc(Cl)cc1)N1C[C@@H](c2ccccc2)C(c2ccc(Cl)cc2)=N1)C(N)=O]  Valine's 2-position CH moiety is CD  (1 deuterium) | L-Valine-2-d$_1$ |
| Q. | 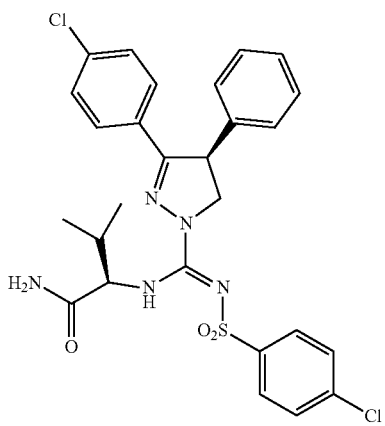 [SMILES: CC(C)[C@@H](N/C(=N\S(=O)(=O)c1ccc(Cl)cc1)N1C[C@H](c2ccccc2)C(c2ccc(Cl)cc2)=N1)C(N)=O]  Valine's 2-position CH moiety is CD  (1 deuterium) | D-Valine-2-d$_1$ |
| R. | 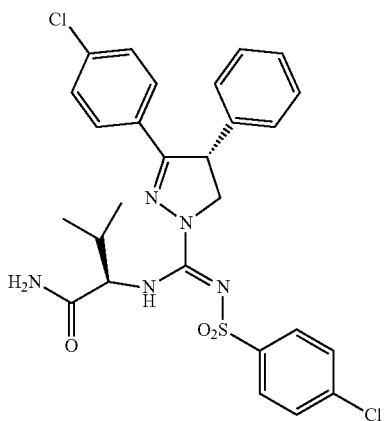  Valine's 2-position CH moiety is CD  (1 deuterium) | D-Valine-2-d$_1$ |

TABLE A-continued
| Ex. # | Deuterium-Enriched Compounds | Deuterated Starting Material |
|---|---|---|
| S. | 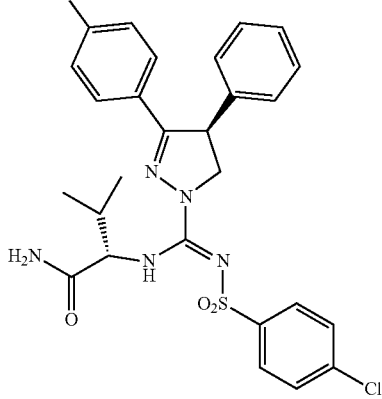  Valine's CHCH(CH$_3$)$_2$ moiety is CDCD(CD$_3$)$_2$ (8 deuteriums) | L-Valine-d$_8$ |
| T. | 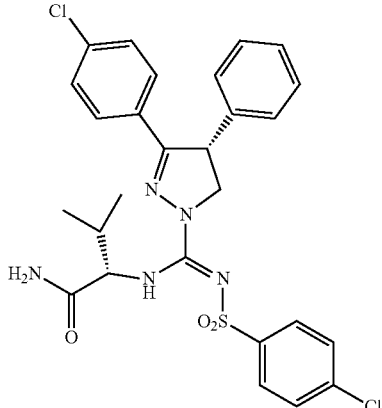  Valine's CHCH(CH$_3$)$_2$ moiety is CDCD(CD$_3$)$_2$ (8 deuteriums) | L-Valine-d$_8$ |
| U. | 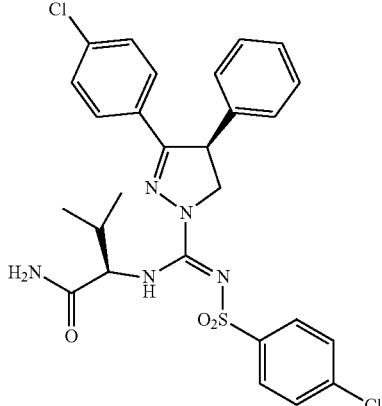  Valine's CHCH(CH$_3$)$_2$ moiety is CDCD(CD$_3$)$_2$ (8 deuteriums) | D-Valine-d$_8$ |

TABLE A-continued

| Ex. # | Deuterium-Enriched Compounds | Deuterated Starting Material |
|---|---|---|
| V. | [chemical structure] Valine's CHCH(CH$_3$)$_2$ moiety is CDCD(CD$_3$)$_2$ (8 deuteriums) | D-Valine-d$_8$ |

In another aspect, the stereometric purity of a desired stereoisomer of the deuterium-enriched compound is at least 60% to about 99.8%, additional examples include 60, 65, 70, 75, 80, 85, 90, 95, 99, 99.1, 99.2, 99.3, 99.4, 99.5, 99.6, 99.7, to about 99.8%.

In another aspect, the present invention provides novel pharmaceutical compositions, comprising: a pharmaceutically acceptable carrier and a therapeutically effective amount of a compound of the present invention or a pharmaceutically acceptable salt form thereof.

In another aspect, the present invention provides novel pharmaceutical compositions, comprising: a pharmaceutically acceptable carrier and a compound of the present invention or a pharmaceutically acceptable salt form thereof.

In another aspect, the present invention provides a novel method of modulating the activity of CB1 receptors (e.g., peripheral CB1 receptors) in a patient, comprising: administering to a patient in need thereof a therapeutically effective amount of a compound of the present invention or a pharmaceutically acceptable salt form thereof.

In another aspect, the present invention provides a novel method of treating a disease characterized by an inappropriate activation of peripheral CB1 receptors, comprising: administering to a patient in need thereof a therapeutically effective amount of a compound of the present invention or a pharmaceutically acceptable salt form thereof.

In another aspect, the present invention provides a novel method for treating a disease mediated by the $CB_1$ receptor in a patient, comprising: administering to a patient in need thereof a therapeutically effective amount of a compound of the present invention or a pharmaceutically acceptable salt form thereof. In an example, the disease is mediated by peripheral $CB_1$ receptors. In another example, the $CB_1$ receptors that are blocked are peripheral $CB_1$ receptors.

In another aspect, the present invention provides a novel method for treating a disease, comprising: administering to a patient in need thereof a therapeutically effective amount of a compound of the present invention or a pharmaceutically acceptable salt form thereof, wherein the disease is selected from obesity, diabetes, dyslipidemias, cardiovascular disorders, inflammatory disorders, hepatic disorders, cancers, and a combination thereof.

In another aspect, the diabetes disorder is selected from Type 1 diabetes, Type 2 diabetes, inadequate glucose tolerance, and insulin resistance.

In another aspect, the dyslipidemia disorder is selected from undesirable blood lipid levels, including low levels of high-density lipoprotein, high levels of low-density lipoprotein, high levels of triglycerides, and a combination thereof.

In another aspect, the cardiovascular disorder is selected from atherosclerosis, hypertension, stroke and heart attack.

In another aspect, the inflammatory disorder is selected from osteoarthritis, rheumatoid arthritis, inflammatory bowel diseases, and obesity-associated inflammation.

In another aspect, the hepatic disorder is selected from liver inflammation, liver fibrosis, non-alcoholic steatohepatitis, fatty liver, enlarged liver, alcoholic liver diseases, jaundice, cirrhosis, and hepatitis.

In another aspect, the cancer is selected from colon, breast, thyroid, and alveolar rhabdomyosarcoma.

In another aspect, the present invention provides a novel method for treating a co-morbidity of obesity, comprising: administering to a patient in need thereof a therapeutically effective amount of a compound of the present invention or a pharmaceutically acceptable salt form thereof.

In another aspect, the co-morbidity is selected from diabetes, dyslipidemias, Metabolic Syndrome, dementia, cardiovascular disease, and hepatic disease.

In another aspect, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the ovaries, cervix, uterus, breasts, prostrate, and gallbladder.

In another aspect, the present invention also provides a method of preventing or reversing the deposition of adipose tissue in a mammal by the administration of a compound of the present invention. By preventing or reversing the deposition of adipose tissue, compound of the present invention are expected to reduce the incidence or severity of obesity, thereby reducing the incidence or severity of associated co-morbidities.

In another aspect, the present invention provides a compound of the present invention for use in therapy.

In another aspect, the present invention provides the use of the present invention for the manufacture of a medicament for the treatment of an indication recited herein (e.g., obesity, diabetes, dyslipidemias, cardiovascular disorders, inflammatory disorders, hepatic disorders, cancers, and a combination thereof).

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

The stereomeric purity of a compound is the stereomeric excess of that specific stereoisomer or stereoisomers (typically called enantiomeric excess when only one stereocenter is present, i.e., two possible stereoisomers). Stereometric purity (SP) is calculated as follows:

$$SP\% = (\text{weight \% Stereoisomer \#1}) - (\text{weight \% of all remaining stereoisomers})$$

Other measureable percentage, such as mole fraction, can also be used to determine SP %. For example, 80% SP refers to 90% by weight of the mixture being Stereoisomer #1 and 10% being Stereoisomer #2 (if one stereocenter) or 10% being Stereoisomers #2-4 (if two stereocenters) or 10% being Stereoisomers #2-8 (if three stereocenters).

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14. Compounds with amino acid side chains containing deuterium for hydrogen on carbon atoms are particularly noteworthy members of this class. Examples of deuterated L-valine as a starting material include: $(CD_3)(CH_3)CHCH(NH_2)CO_2H$, $(CD_3)(CD_3)CHCH(NH_2)CO_2H$, $(CH_3)(CH_3)CHCD(NH_2)CO_2H$, $(CD_3)(CD_3)CHCD(NH_2)CO_2H$, and $(CD_3)_2CDCD(NH_2)CO_2H$. Examples of deuterated L-serinamide as a starting material include: $HOCD_2CH(NH_2)CONH_2$, $HOCH_2CD(NH_2)CONH_2$, and $HOCD_2CD(NH_2)CONH_2$. Examples of deuterated L-threoninamide as a starting material include: $CD_3CH(OH)CH(NH_2)CONH_2$, $CH_3CD(OH)CH(NH_2)CONH_2$, $CH_3CH(OH)CD(NH_2)CONH_2$, and $CD_3CD(OH)CD(NH_2)CONH_2$. Examples of deuterated amino-acetamide as a starting material include: $H_2NCHDCONH_2$ and $H_2NCD_2CONH_2$.

"Mammal" and "patient" cover warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycoloylarsanilic, hexylresorcinol, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat obesity, diabetes, dyslipidemias, cardiovascular disorders, inflammatory disorders, hepatic disorders, cancers, and a combination or comorbidity thereof, or another indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Overweight is defined as having a BMI≥25. Obesity is associated with an increase in the overall amount of adipose tissue (i.e., body fat), especially adipose tissue localized in the abdominal area. Obesity has reached epidemic proportions in the United States. The prevalence of obesity has steadily increased over the years among all racial and ethnic groups. In 2012 the Centers for Disease Control and Prevention reports that 35.7% of adults in the U.S. are obese. Even more alarming, 17% of children and adolescents aged 2-19 are obese. This translates to more than 50 million Americans identified as obese. Obesity is responsible for more than 300,000 deaths annually, and will soon overtake tobacco usage as the primary cause of preventable death in the United States. Obesity is a chronic disease that contributes directly to numerous dangerous co-morbidities, including type 2 diabetes, cardiometabolic diseases, hepatic disorders, cardiovascular disease, inflammatory diseases, premature aging, and some forms of cancer.

Drugs currently approved for the treatment of obesity fall into two categories: (a) CNS appetite suppressants such as phentermine, lorcaserin, and a topiramate/phentermine combination, and (b) gut lipase inhibitors such as orlistat. CNS appetite suppressants reduce eating behavior through activation of the 'satiety center' in the brain and/or by inhibition of the 'hunger center' in the brain. Gut lipase inhibitors reduce the absorption of dietary fat from the gastrointestinal (GI) tract. Although appetite suppressants and gut lipase inhibitors work through very different mechanisms, they share in common the same overall goal of reducing body weight secondary to reducing the amount of calories that reach the systemic circulation. Unfortunately, these indirect therapies produce only a modest initial weight loss (approximately 5% compared to placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life. The lack of therapeutic effectiveness, coupled with the spiraling obesity epidemic, positions the 'treatment of obesity' as one of the largest and most urgent unmet medical needs. There is, therefore, a real and continuing need for the development of improved medications that treat or prevent obesity.

It is desirable to treat overweight or obese patients by reducing their amount of adipose tissue, and thereby reducing their overall body weight to within the normal range for their sex and height. In this way, their risk for co-morbidities such as diabetes, dyslipidemias, cardiovascular disorders, inflammatory disorders, hepatic disorders, and cancers will be reduced. It is also desirable to prevent normal weight individuals from accumulating additional, excess adipose tissue, effectively maintaining their body weights at a BMI<25, and preventing the development of co-morbidities. It is also desirable to control obesity, effectively preventing overweight and obese individuals from accumulating additional, excess adipose tissue, reducing the risk of further exacerbating their co-morbidities.

The World Health Organization definition of diabetes is for a single raised glucose reading with symptoms otherwise raised values on two occasions, of either fasting plasma glucose≥7.0 mmol/l (126 mg/dl) or with a Glucose tolerance test: two hours after the oral dose a plasma glucose≥11.1 mmol/l (200 mg/dl). Type 2 Diabetes is rapidly increasing in the developed world and there is some evidence that this pattern will be followed in much of the rest of the world in coming years. CDC has characterized the increase as an epidemic, with more than 25.8 million Americans diagnosed with diabetes, and another 79 million identified as prediabetic (National Diabetes Facts Sheet, released January, 2011). In addition, whereas this disease used to be seen primarily in adults over age 40 (in contrast to Diabetes mellitus type 1), it is now increasingly seen in children and adolescents, an increase thought to be linked to rising rates of obesity in this age group.

Type 2 Diabetes or Diabetes mellitus type 2 or (formerly called non-insulin-dependent diabetes mellitus (NIDDM), or adult-onset diabetes) is a metabolic disorder that is primarily characterized by insulin resistance, relative insulin deficiency, glucose intolerance, and/or hyperglycemia. Insulin resistance means that body cells do not respond appropriately when insulin is present. Unlike insulin-dependent diabetes mellitus (Type 1), the insulin resistance is generally "post-receptor", meaning it is a problem with the cells that respond to insulin rather than a problem with insulin production. Type 2 diabetes is presently of unknown etiology (i.e., origin). About 90-95% of all North American cases of diabetes are type 2, and about 20% of the population over the age of 65 has diabetes mellitus Type 2 (*Nature*, 2001, 414, 6865). The majority of type 2 diabetics are obese, and chronic obesity leads to increased insulin resistance that can develop into diabetes (*Morbidity and Mortality Weekly Report* 2008, 53, 1066). Type 2 diabetes is often associated with obesity, hypertension, elevated cholesterol (combined hyperlipidemia), and with the condition often termed Metabolic syndrome (it is also known as Syndrome X, Reavan's syndrome, or CHAOS). There are several drugs available for Type 2 diabetics, including metformin, thiazolidinediones, which increase tissue insulin sensitivity, α-glucosidase inhibitors which interfere with absorption of some glucose containing nutrients, and peptide analogs that must be injected.

Dyslipidemia is the presence of abnormal levels of lipids and/or lipoproteins in the blood. Lipids (fatty molecules) are transported in a protein capsule, and the density of the lipids and type of protein determines the fate of the particle and its influence on metabolism. Lipid and lipoprotein abnormalities are extremely common in the general population, and are regarded as a highly modifiable risk factor for cardiovascular disease due to the influence of cholesterol, one of the most clinically relevant lipid substances, on atherosclerosis. In addition, some forms may predispose to acute pancreatitis.

In western societies, most dyslipidemias are hyperlipidemias; that is, an elevation of lipids in the blood, often due to diet and lifestyle. The prolonged elevation of insulin levels can also lead to dyslipidemia. The most prevalent hyperlipidemias include: hypercholesterolemia, characterized by elevated cholesterol (usually LDL), hypertriglyceridemia, characterized by elevated triglycerides (TGs); hyperlipoproteinemia, characterized by elevated lipoproteins; hyperchylomicronemia, characterized by elevated chylomicrons; and combined hyperlipidemia, characterized by elevated LDL and triglycerides. Abnormal decreases in the levels of lipids and/or lipoproteins in the blood also can occur. These include hypocholesterolemia, characterized by lowered cholesterol (usually high density lipoprotein, or HDL); and abetalipoproteinemia, characterized by lowered beta lipoproteins.

Dyslipidemia contributes to the development of atherosclerosis. Causes may be primary (genetic) or secondary. Diagnosis is by measuring plasma levels of total cholesterol, TGs, and individual lipoproteins. Treatment is dietary changes, exercise, and lipid-lowering drugs. A linear relation probably exists between lipid levels and cardiovascular risk, so many people with "normal" cholesterol levels benefit from achieving still lower levels. Normal and abnormal lipid levels have been defined in the Third Report of the Expert Panel on Detection, Evaluation, and Treatment of High Blood Cholesterol in Adults. National Institutes of Health, National Heart, Lung, and Blood Institute, 2001.

The treatment of choice for dyslipidemias is lifestyle change, including diet and exercise. Drugs are the next step when lifestyle changes are not effective. Lipid lowering drugs include statins, nicotinic acid, bile acid sequestrants, fibrates, cholesterol absorption inhibitors, and combination treatments (e.g., niacin and a statin). These agents are not without adverse effects, including flushing and impaired glucose tolerance (nicotinic acid), bloating, nausea, cramping, and constipation (bile acid sequestrants). Bile acid sequestrants may also increase TGs, so their use is contraindicated in patients with hypertriglyceridemia. Fibrates potentiate muscle toxicity when used with statins, and may increase LDL in patients with high TGs.

There are many kinds of hepatic (i.e., liver) diseases. Viruses cause some of them, like hepatitis A, hepatitis B and hepatitis C. Others can be the result of drugs, poisons or drinking too much alcohol. If the liver forms scar tissue because of an illness, it's called cirrhosis. Jaundice, or yellowing of the skin, can be one sign of hepatic disease. Cancer can affect the liver. Hepatic diseases such as hemochromatosis can be inherited. Additional liver diseases include nonalcohol steatohepatitis (NASH), alcoholic liver disease, cholangiocarcinoma, hepatic encephalopathy, hepatic failure, liver abscess, liver tumors, liver coagulopathy, glycogen storage diseases, portal hypertension, primary biliary cirrhosis, and primary sclerosing cholangitis.

There are few good treatment options for liver diseases. Options include lifestyle change (including diet and exercise), liver transplantation, and insertion of a transjugular intrahepatic portosystemic shunt that is placed in veins in the middle of the liver to improve blood flow to and from the organ. There are few effective drug treatment options for hepatic diseases. Interferon is an FDA-approved drug for the treatment of viral hepatitis. The chimeric protein Hyper-IL-6 dramatically enhances hepatocyte proliferation and is currently being evaluated as a pharmacological treatment for liver injury.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms (J. Clin. Invest. 1996, 97, 2517) are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport (J. Clin. Invest. 1996, 97, 2517). Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics. These include antihistamines (Drug Metab. Dispos. 2003, 31, 312), beta-adrenergic receptor antagonists (Eur. J. Clin. Pharmacol. 1985, 28, Suppl: 21; Br. J. Clin. Pharmacol., 1981, 11, 549), non-nucleoside reverse transcriptase inhibitors (NNRTIs, J. Pharm. Sci., 1999, 88, 950), and opioid antagonists. This latter group has been tested in relation to their activity in the gastrointestinal tract. These peripherally selective opioid antagonists are described in various U.S. patents as being useful in the treatment of non-CNS pathologies in mammals, in particular those of the gastrointestinal tract [see U.S. Pat. Nos. 5,260,542; 5,434,171; 5,159,081; and 5,270,238].

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid-induced gastrointestinal side effects associated with opioid administration (J. Pharmacol. Exp. Ther. 2002, 300, 118).

The discovery that the anti-obesity activity of cannabinoid receptor blockers is in part mediated by a non-CNS mechanism makes it beneficial for the compounds of the present invention to be peripherally restricted (i.e., have an inability or limited ability to cross the BBB, or be readily eliminated from the brain through active transport systems). It may be desirable for the compounds of the present invention to be peripherally restricted, which in turn will result in no or very limited CNS effects. Compounds that provide peripherally mediated efficacy in treating obesity, diabetes, dyslipidemias, cardiovascular disorders, inflammatory disorders, hepatic disorders, cancers, a comorbidity thereof, or a combination or should result in therapeutic agents with greater safety. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects, or both.

Compounds of the present invention have been shown to be active cannabinoid receptor blockers (e.g., have activity at ≤10 μM). The compounds of the present invention are typically CB1 cannabinoid receptor blockers. However, CB1 blockers frequently are also CB2 blockers (i.e., CB2 antagonists or inverse agonists). Thus the present invention also includes CB2 blockers and compounds that are both CB1 and CB2 blockers.

An inverse agonist is a compound that not only blocks the action of the endogenous agonist at the receptor, but also exhibits its own activity which is usually the opposite of that shown by the agonist. Inverse agonists are also effective against certain types of receptors (e.g. certain histamine receptors/GABA receptors) that have intrinsic activity without the interaction of a ligand upon them (also referred to as 'constitutive activity').

Most methods of treating obesity are dependent on a significant reduction in energy intake, either by a decrease in food intake (e.g., lorcaserin) or by inhibition of fat absorption (e.g., orlistat). In the present invention, adipose tissue may be reduced in the absence of a significant reduction in food intake. The weight loss, as a result of the present invention, comes from the treatment with a compound of the present invention, largely independent of, though not totally dissociated from, appetite and food intake. It can be desirable that adipose tissue loss occurs while food intake is maintained, increased or (a) about 1, 2, 3, 4, 5, 6, 7, 8, 9, 10, 11, 12, 13, 14, 15, 16, 17, 18, 19, or 20% below the normal range of the subject prior to being treated in accordance with the present invention (i.e., its pre-administration level), (b) about 1, 2, 3, 4, 5, 6, 7, 8, 9, 10, 11, 12, 13, 14, or 15% below its pre-administration level, (c) about 1, 2, 3, 4, 5, 6, 7, 8, 9, or 10% below its pre-administration level, or (d) about 1, 2, 3, 4, or 5% below its pre-administration level.

In some cases, loss of adipose tissue can be accompanied by a concomitant loss of lean muscle mass. This is particularly evident in cancer patients who show a generalized wasting of body tissues, including adipose tissue and lean muscle mass. In the present invention, however, it can be desirable for body fat to be significantly reduced in the absence of a significant reduction in lean body mass. Adipose tissue loss comes from treatment with a compound of the present invention, independent of a significant change in lean body mass. Thus, adipose tissue loss can occur while lean body mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

In some cases, loss of adipose tissue can be accompanied by a concomitant loss of water mass. This is particularly evident with diet regimens that promote dehydration. In the present invention, it can be desirable for body fat to be significantly reduced in the absence of a significant reduction in water mass. In other words, adipose tissue loss comes from treatment with a compound of the present invention, independent of a significant change in water mass. It can be desirable that adipose tissue loss occurs while water mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

Phentermine and orlistat are currently marketed for use in the treatment of obesity, albeit weight loss is achieved through entirely different mechanism of action. Phentermine inhibits appetite via a direct brain action, and orlistat inhibits gut lipase enzymes that are responsible for breaking down ingested fat.

Cannabinoid receptor blockers can promote weight loss through inhibition of peripheral cannabinoid receptors, a mechanism entirely different from direct brain appetite suppressants, gut lipase inhibitors, and other agents with similar indications (e.g., serotonin agonists, fatty acid synthase inhibitors, and monoamine oxidase (MAO) inhibitors). Co-administration of a cannabinoid receptor blocker together with one or more other agents that are useful for treating the indications described above (e.g., obesity, diabetes, dyslipidemias, cardiovascular disorders, inflammatory disorders, hepatic disorders, cancers, and a combination thereof) is expected to be beneficial, by producing, for example, either additive or synergistic effects. Examples of additional agents include an appetite suppressant, a lipase inhibitor, and a MAO inhibitor (e.g., MAO-B and a combination of MAO-A/B). Therefore, the present invention provides a method of treating obesity, diabetes, dyslipidemias, cardiovascular disorders, inflammatory disorders, hepatic disorders, and/or cancers, and a combination thereof, comprising administering a therapeutically effective amount of a compound of the present invention and a second component effective for treating the desired indication.

Examples of second components include anti-obesity agents, which include, but are not limited to:1) growth hormone secretagogues; 2) growth hormone secretagogue receptor agonists/antagonists; 3) melanocortin agonists; 4) Mc4r (melanocortin 4 receptor) agonists; 5) .beta.−3 agonists; 7) 5HT2C (serotonin receptor 2C) agonists; 8) orexin antagonists; 9) melanin concentrating hormone antagonists; 10) melanin-concentrating hormone 1 receptor (MCH$_1$R) antagonists; 11) melanin-concentrating hormone 2 receptor (MCH$_2$R) agonist/antagonists; 12) galanin antagonists; 13) CCK agonists; 14) CCK-A (cholecystokinin-A) agonists; 16) corticotropin-releasing hormone agonists; 17) NPY 5 antagonists; 18) NPY 1 antagonists; 19) histamine receptor-3 (H3) modulators; 20) histamine receptor-3 (H3) blockers; 21)β-hydroxy steroid dehydrogenase-1 inhibitors (.beta.-HSD-1); 22) PDE (phosphodiesterase) inhibitors; 23) phosphodiesterase-3B (PDE3B) inhibitors; 24) NE (norepinephrine) transport inhibitors; 25) non-selective serotonin/norepinephrine transport inhibitors, such as sibutramine, phentermine, or fenfluramine; 26) ghrelin antagonists; 28) leptin derivatives; 29) BRS3 (bombesin receptor subtype 3) agonists; 30) CNTF (Ciliary neurotrophic factors); 31) CNTF derivatives, such as axokine (Regeneron); 32) monoamine reuptake inhibitors; 33) UCP-1 (uncoupling protein-1), 2, or 3 activators; 34) thyroid hormone .beta. agonists; 35) FAS (fatty acid synthase) inhibitors; 37) DGAT2 (diacylglycerol acyltransferase 2) inhibitors; 38) ACC2 (acetyl-CoA carboxylase-2) inhibitors; 39) glucocorticoid antagonists; 40) acyl-estrogens; 41) lipase inhibitors, such as orlistat (Xenical®); 42) fatty acid transporter inhibitors; 43) dicarboxylate transporter inhibitors; 44) glucose transporter inhibitors; 45) phosphate transporter inhibitors; 46) serotonin reuptake inhibitors; 47) Metformin (Glucophage®); 48) Topiramate (Topimax®); 49) opiate antagonists such as naltrexone, 50) the non-selective transport inhibitor bupropion, and/or 51) MAO inhibitors.

Examples of MAO inhibitors include Moclobemide; Brofaromine; BW A616U; Ro 41-1049; RS-2232; SR 95191; Harmaline; Harman; Amiflamine; BW 1370U87; FLA 688; FLA 788; Bifemelane; Clorgyline; LY 51641; MDL 72,394; 5-(4-Benzyloxyphenyl)-3-(2-cyanoethyl)-(3H)-1,3,4-oxadiazol-2-one; 5-(4-Arylmethoxyphenyl)-2-(2-cyanoethyl)tetrazoles; Lazabemide; Ro 16-6491; Almoxatone; XB308; RS-1636; RS-1653; NW-1015; SL 340026; L-selegiline; Rasagiline; Pargyline; AGN 1135; MDL 72,974; MDL 72,145; MDL 72,638; LY 54761; MD 780236; MD 240931; Bifemelane; Toloxatone; Cimoxatone; Iproniazid; Phenelzine; Nialamide; Phenylhydrazine; 1-Phenylcyclopropylamine; Isocarboxazid; and, Tranylcypromine. Additional examples of MAO inhibitors can be found in USPA 2007/0004683; USAN Ser. No. 11/445,044; USPA 2007/0015734; and USAN Ser. No. 11/424,274.

Examples of diabetes disorders include treating Type 1 diabetes, Type 2 diabetes, inadequate glucose tolerance, and insulin resistance.

Examples of second components useful for treating diabetes include (a) insulin sensitizers including (i) PPAR-γ agonists such as the glitazones (e.g. troglitazone, pioglitazone, englitazone, MCC-555, rosiglitazone), and compounds disclosed in WO97/27857, 97/28115, 97/28137, and 97/27847; and (ii) biguanides such as metformin and phenformin; (b) insulin or insulin mimetics; (c) sulfonylureas such as tolbutamide and glipizide, or related materials; (d) α-glucosidase inhibitors (e.g., acarbose); (e) cholesterol lowering agents such as (i) HMG-CoA reductase inhibitors (lovastatin, simvastatin, pravastatin, fluvastatin, atorvastatin, rivastatin, and other statins), (ii) sequestrants (e.g., cholestyramine, colestipol, and dialkylaminoalkyl derivatives of a cross-linked dextran), (iii) nicotinyl alcohol, nicotinic acid or a salt thereof, (iv) PPAR-αagonists (e.g., fenofibric acid derivatives including gemfibrozil, clofibrate, fenofibrate, and bezafibrate), (v) inhibitors of cholesterol absorption (e.g., β-sitosterol) and acyl CoA:cholesterol acyltransferase inhibitors (e.g., melinamide), and (vi) probucol; (f) PPAR-α/γ agonists; (g) antiobesity compounds (described previously); (h) ileal bile acid transporter inhibitors; (i) insulin receptor activators, (j) dipeptidyl peptidase IV, or DPP-4 inhibitors (sitagliptin, vildagliptin and other DPP-4 inhibitors (k) exenatide, (1) pramLintide, (m) FBPase inhibitors, (n) glucagon receptor antagonists, (o) glucagon-like peptide-1, and (p) the glucagon-like peptide-1 analogues (liraglutide, and others).

The compounds of the present invention are expected to be CB1 receptor blockers and are expected to be useful for treating diseases mediated by the $CB_1$ receptor. The compounds of the present are expected to possess an affinity in vitro for the central and/or peripheral cannabinoid receptors under the experimental conditions described by Devane et al., *Molecular Pharmacology*, 1988, 34, 605-613. The compounds according to the invention are also expected to possess an affinity for the cannabinoid receptors present on preparations of electrically stimulated isolated organs. These tests can be performed on guinea-pig ileum and on mouse vas deferens according to Roselt et al., *Acta Physiologica Scandinavia* 1975, 94, 142-144, and according to Nicolau et al., *Arch. Int. Pharmacodyn*, 1978, 236, 131-136.

CB1 receptor affinities can be determined using membrane preparations of Chinese hamster ovary (CHO) cells in which the human cannabinoid CB1 receptor is stably transfected (*Biochem J.* 1991, 279, 129-134) in conjunction with [3H]CP-55,940 as radioligand. After incubation of a freshly prepared cell membrane preparation with the [3H]-radioligand, with or without addition of test compound, separation of bound and free ligand is performed by filtration over glass fiber filters. Radioactivity on the filter is measured by liquid scintillation counting. The $IC_{50}$ values can be determined from at least three independent measurements.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal); subdermal implants; and, buccal, sublingual, topical, rectal, vaginal, and intranasal administrations. Bioerodible, non-bioerodible, biodegradable, and non-biodegradable systems of administration may also be used. Examples of oral formulations include tablets, coated tablets, hard and soft gelatin capsules, solutions, emulsions, and suspensions.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the compound of the present invention administered daily will vary on an individual basis and to some extent may be determined by the severity of the disease being treated (e.g., obesity, diabetes, liver diseases, cardiometabolic disorders, and cancers). The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Solution |
|---|---|
| Active substance | 1.0 mg |
| 1N HCl | 20.0 μl |
| acetic acid | 0.5 mg |
| NaCl | 8.0 mg |
| Phenol | 10.0 mg |
| 1N NaOH | q.s. ad pH 5 |
| H$_2$O | q.s. ad 1 mL |

SYNTHESIS

The compounds of the present invention can be prepared in a number of ways known to one skilled in the art of organic synthesis (e.g., see U.S. Pat. No. 6,476,060 B2, *J Med Chem* 2004, 47, 627). The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Other features of the invention will become apparent in the course of the following descriptions of exemplary embodiments that are given for illustration of the invention and are not intended to be limiting thereof.

EXAMPLES

The following examples are representative of the procedures used to prepare the preferred compounds in this application.

Example 1

The pyrazoline starting material was prepared according to the procedures previously described [see *J. Agric. Food Chem.*, 27, 406 (1979); *J. Med Chem.*, 47, 627(2004)]. Condensation with N-[4-chlorophenyl)sulfonyl]carbamic acid methyl ester, obtained from the appropriately substituted sulfonamide and methyl chloroformate as previously described gave the sulfonylurea shown below.

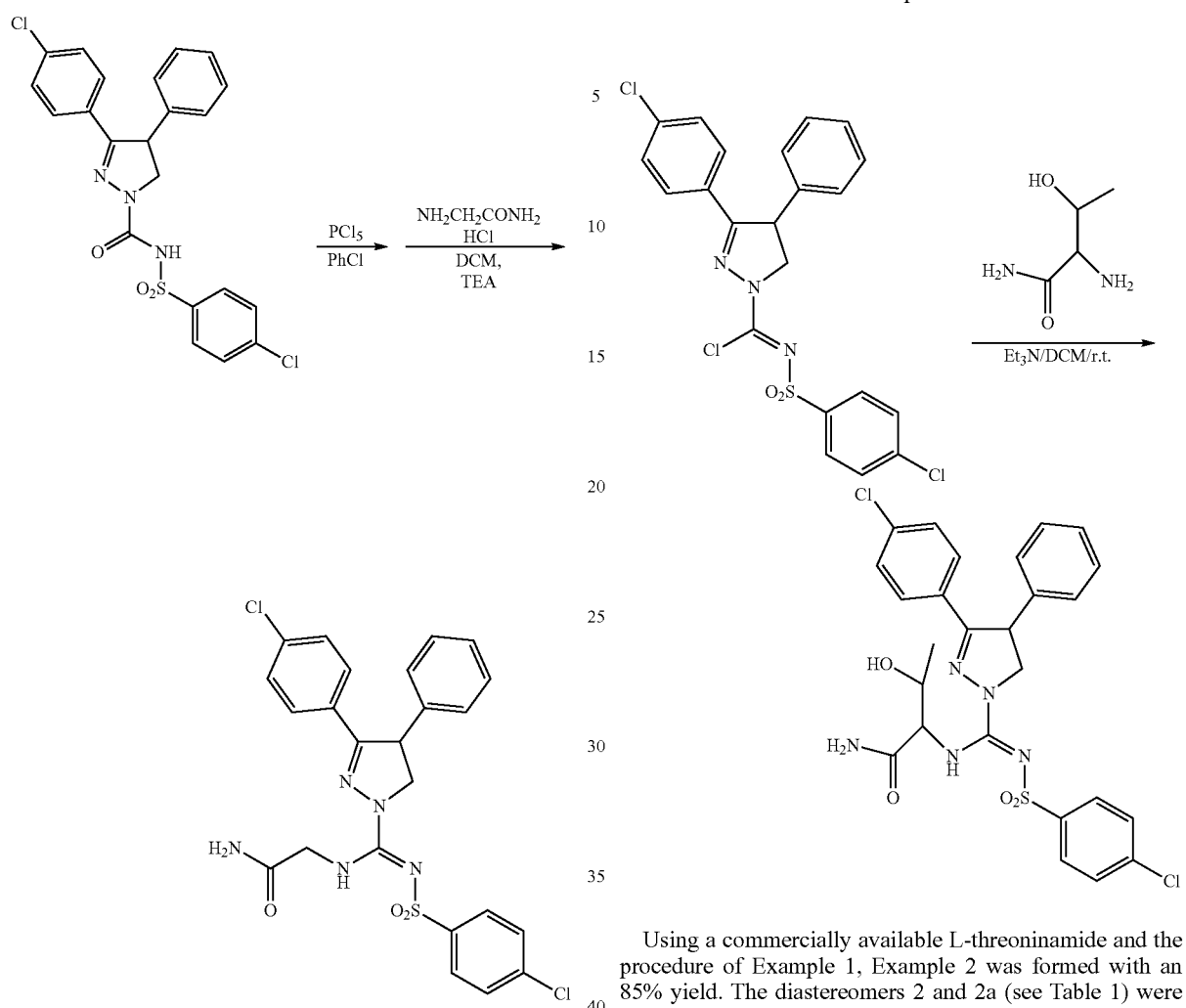

A mixture of 10 g sulfonylurea (1) and PCl₅ (6.6 g, 1.5 eq) in 120 mL chlorobenzene was reflux for 1.5 hours. The volume of the solvent was reduced to about 20-30 mL in vacuo, and the imidoyl chloride mixture was used in the subsequent reaction.

To NH₂CH₂CONH₂ HCl salt 4.67 g (2.0 eq) in 50 mL DCM cooled in ice-water bath, was added 9.64 g (4.5 eq) of TEA followed by the drop wise addition of above imidoyl chloride mixture over a 10-15 min period. The reaction mixture was stirred at this temperature for 0.5 h, then ambient temperature for an additional two hours. After evaporation of the solvent, the residue was dissolved in ice-water, extracted three times with ethyl acetate (200 mL+100 mL+50 mL), and the combined extracts were dried with anhydrous Na₂SO₄. Evaporation of the solvent and purification using silica gel flash chromatography (ethyl acetate/petroleum ether (1/1) afforded the appended carboxamide.

The R and S enantiomers of Example 1 were isolated using a CHIRALPAK IC column (an immobilized polysaccharide chiral stationary phase) and MeOH as the eluent (mobile phase) at 35° C.

Example 2

Using a commercially available L-threoninamide and the procedure of Example 1, Example 2 was formed with an 85% yield. The diastereomers 2 and 2a (see Table 1) were separated using a CHIRALCEL OD-H 5μ column, 30% methanol/70% CO₂ as eluents; 35° C.

Examples 2b-c can be formed using the unnatural D-threoninamide.

Examples 2d-g can be formed using the appropriate L- and D-allo-threoninamide.

Example 3

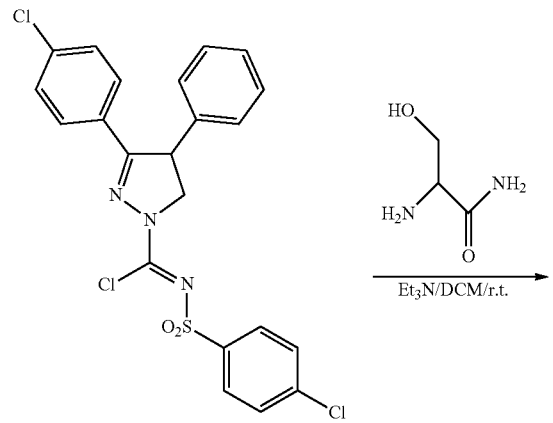

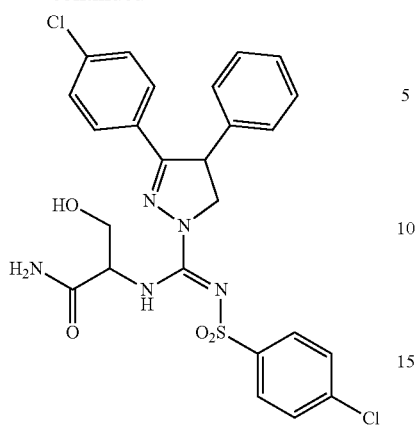

Using a commercially available starting L-serinamide and the procedure of Example 1, Example 3 was formed with a 40% yield. The diastereomers 3 and 3a (see Table 1) were separated at using a CHIRALPAK IC-H 5μ column, 95% acetonotrile/5% methanol as eluents, ambient temperature.

Examples 3b-c can be formed using the unnatural D-serinamide.

Example 4

The pyrazoline starting material was prepared according to the procedures previously described [see *J. Agric. Food Chem.*, 27, 406 (1979); *J. Med Chem.*, 47, 627(2004)]. Condensation with the N-[4-chlorophenyl)sulfonyl]carbamic acid methyl ester, obtained from the appropriately substituted sulfonamide and methyl chloroformate as previously described gave the 4,5-dihydropyrazole-1-carboxamide, and chlorination of this product with phosphorus pentachloride in chlorobenzene at reflux produced the imidoylchloride.

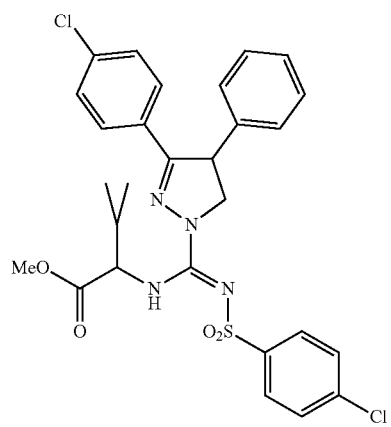

To 10 mmoles of imidoyl chloride suspended in 20 mL of dichloromethane (DCM) was added dropwise to a cooled solution of 12 mmols of L-valine methyl ester hydrochloride salt and 25 mmoles of triethylamine in 50 mL DCM. After the addition, the reaction mixture was allowed to warm to ambient temperature and stirred for about one hour. The solvent was removed in vacuo and water (50 mL) was added and the mixture was extracted with EtOAc. The combined extracts were washed with brine, and then dried over anhydrous $Na_2SO_4$. After solvent removal in vacuo the residue was purified by silica gel column chromatogram (PE/EtOAc: 2/1) to afford the carboxamidine. Conversions of this ester to the carboxylic acid and the corresponding carboxamide were carried out via conventional methodology as described below.

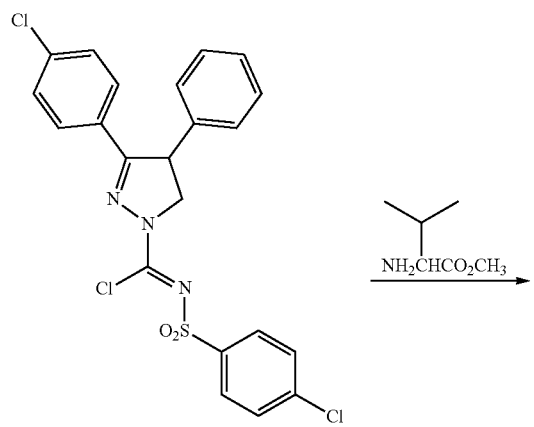
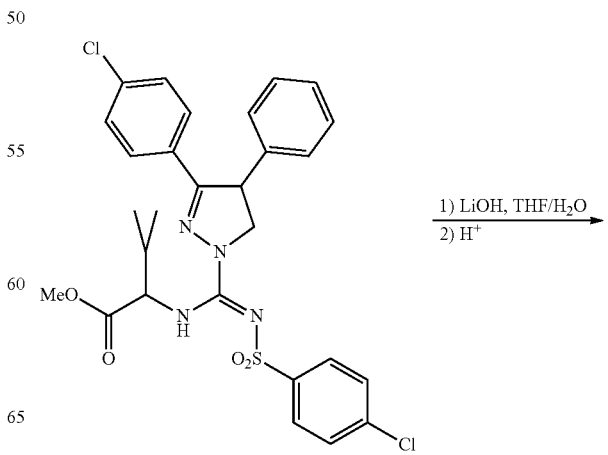

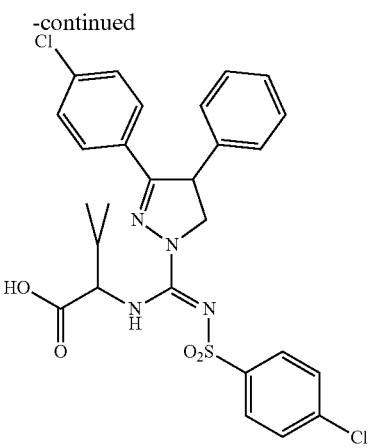

The L-valine ester adduct 20.85 g (35.49 mmol)(1.0 eq) was stirred at ~15° C. in the aqueous (30 mL H$_2$O) THF (90 mL) solution containing 3 equivalents of LiOH (4.472 g)(106.5 mmol) for 14 hrs. The solvents were removed under reduced pressure and 100 mL of water and 300 mL ethyl acetate were added to the residue. The pH of the aqueous solution was adjusted to ~1-2 with 15% HCl solution, and the organic layer was separated. After additional extractions with ethyl acetate, the combined extracts were washed with brine and dried over Na$_2$SO$_4$. The product was purified by silica gel chromatography (DCM and MeOH). Yield: 21.4 g, 85%.

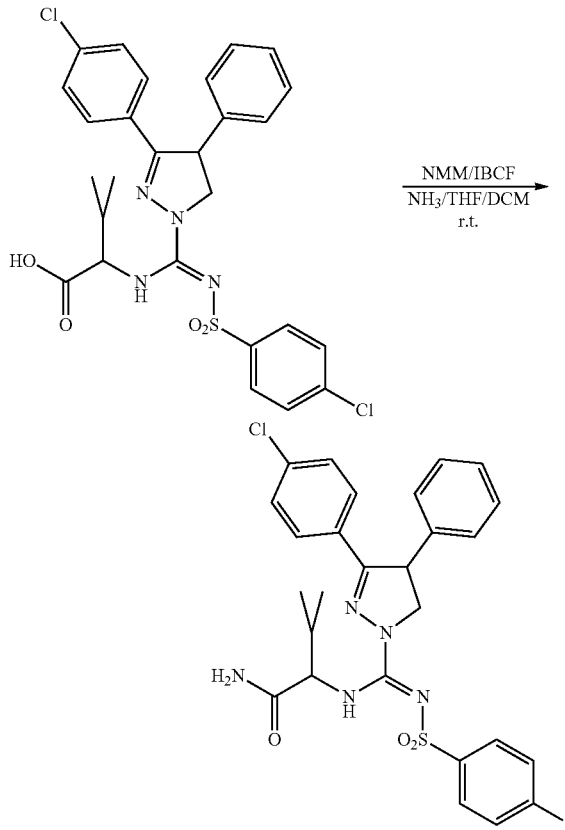

The L-valine adduct 21.4 g (37.3 mmol, 1.0 e.q.) in dichloromethane (DCM) (150 mL) containing N-methylmorpholine (NMM) 13.191 g (131 mmol, 3.5 e.q.) was mixed and cooled to −10° C. A solution of isobutyl chloroformate (IBCF) 5.604 g (41.1 mmol, 1.1 e.q.) in DCM (50 mL) was slowly added, and the reaction mixture was stirred for ~30 minutes after addition. A solution of NH$_3$ in THF solution (~2N)(700 mL) was then added, and the mixture was stirred for additional 30 mins at −5° C., and then 1-3 hrs at ambient temperature. The reaction mixture was concentrated and 100 mL water and 350 mL EtOAc (EA) were added to the residue. The organic layer was separated and the aqueous phase was extracted with additional portions of EA. The combined extracts were washed with brine and dried over Na$_2$SO$_4$. Solvent removal gave the crude product which was dissolved into a minimal amount of DCM followed by the careful addition petroleum ether (PE) until no further solid precipitated. The solid was collected by filtration and dried under vacuum. Yield: 9.745 g, 50%. Recrystallization afforded material with a high de (vide infra).

$^1$H NMR (CDCl$_3$): 1.15, 1.18 6H, d, CH$_3$; 2.43 1H brd s CH; 4.12, 1H, brd s, CH; 4.45, 1H, t, CH; 4.68, 2H, brd s, CH; 7.11, 7.13, 2H, aromatic Hs; 7.19-7.30, 5H, aromatic Hs; 7.47-7.50, 2H, aromatic Hs; 7.57-7.60, 2H, aromatic Hs; 7.87-7.90, 2H, aromatic Hs.

The absolute stereochemical configuration of Example 4 as the S,S diastereomer was determined by x-ray diffraction. Example 4 was dissolved in small amount of isopropanol and then methylene chloride was added. The solution was kept at room temperature overnight to give small crystals. After two days at room temperature larger crystals were obtained. Single-crystal X-ray diffraction data on Example 4 was collected using CuKa radiation and a Bruker Platinum 135 CCD area detector. A 0.023×0.079×0.129 mm$^3$ crystal was prepared for data collection by coating with high viscosity microscope oil. The oil-coated crystal was mounted on a micro-mesh mount (Mitergen, Inc.) and transferred to the diffractometer and data collected at room temperature. The crystal was monoclinic in space group C 2, with unit cell dimensions a=19.9407(7), b=5.4435(2), c=25.1138(9) Å, and b=90.523(2)°. Data was 95.5% complete to 68.33° q (approximately 0.83 Å) with an average redundancy of 2.80. The final anisotropic full matrix least-squares refinement on F$^2$ with 345 variables converged at R1=4.91%, for the observed data and wR2=15.32% for all data. The structure was solved by direct methods and refined by full-matrix least squares on F$^2$ values using the programs found in the SHELXTL suite (Bruker, SHELXTL v6.10, 2000, Bruker AXS Inc., Madison, Wis.). Corrections were applied for Lorentz, polarization, and absorption effects. Parameters refined included atomic coordinates and anisotropic thermal parameters for all non-hydrogen atoms. Hydrogen atoms on carbons were included using a riding model [coordinate shifts of C applied to H atoms] with C—H distance set at 0.96 Å.

Alternatively, the diastereomeric mixture of Example 4 and 4a can be separated on a CHIRALPAK AS-H, 5μ eluting with 30% methanol/70% CO$_2$, 35° C.

Examples 4b-c can be formed using the unnatural D-valine.

Table 1 shows the structures of compounds of the present invention that can be synthesized as described above. Compound binding to CB$_1$R was assessed in competition displacement assays using [$_3$H]CP-55,940 as the radioligand and crude membranes from mouse brain. See Tam, J., Vemuri, V. K., Liu, J., Batkai, S., Mukhopadhyay, B., Godlewski, G., Osei-Hyiaman, D., Ohnuma, S., Ambudkar, S. V., Pickel, J., et al., *J. Clin. Invest.* 2010, 120, 2953-2966.

All data were in triplicates with Ki values determined from three independent experiments.

The CB$_1$ IC$_{50}$ values for tested compounds are as follows.

+ >1000 nM
++ >500-1,000 nM
+++ 100-500 nM
++++ <100 nM

TABLE 1

| Ex. # | Structure | CB1 IC$_{50}$ |
|---|---|---|
| 1 (4'S) | 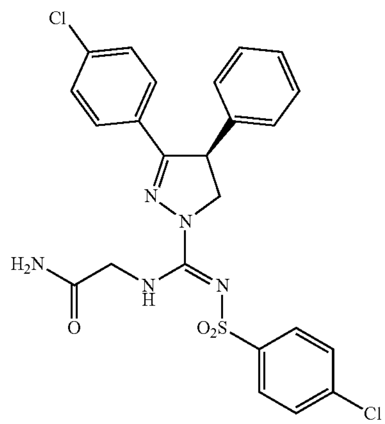 [SMILES: NC(=O)CN/C(=N\S(=O)(=O)c1ccc(Cl)cc1)N1C[C@H](c2ccccc2)C(c2ccc(Cl)cc2)=N1] | ++++ |
| 1a (4'R) | 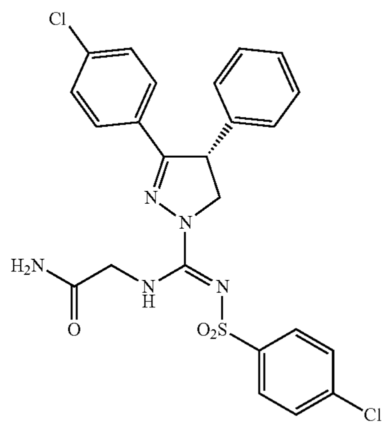 [SMILES: NC(=O)CN/C(=N\S(=O)(=O)c1ccc(Cl)cc1)N1C[C@@H](c2ccccc2)C(c2ccc(Cl)cc2)=N1] | + |
| 2 (2S,3R,4'S) | (2S,3R)-2-((S)-3-(4-chlorophenyl)-N'-((4-chlorophenyl)sulfonyl)-4-phenyl-4,5-dihydro-1H-pyrazole-1-carboximidamido)-3-hydroxybutanamide | ++++ |
| 2a (2S,3R,4'R) | (2S,3R)-2-((R)-3-(4-chlorophenyl)-N'-((4-chlorophenyl)sulfonyl)-4-phenyl-4,5-dihydro-1H-pyrazole-1-carboximidamido)-3-hydroxybutanamide | + |
| 2b (2R,3R,4'S) | (2R,3R)-2-((S)-3-(4-chlorophenyl)-N'-((4-chlorophenyl)sulfonyl)-4-phenyl-4,5-dihydro-1H-pyrazole-1-carboximidamido)-3-hydroxybutanamide | |
| 2c (2R,3R,4'R) | (2R,3R)-2-((R)-3-(4-chlorophenyl)-N'-((4-chlorophenyl)sulfonyl)-4-phenyl-4,5-dihydro-1H-pyrazole-1-carboximidamido)-3-hydroxybutanamide | |

TABLE 1-continued

| Ex. # | Structure | CB1 IC50 |
|---|---|---|
| 2d (2S,3S,4'S) | (2S,3S)-2-((S)-3-(4-chlorophenyl)-N'-((4-chlorophenyl)sulfonyl)-4-phenyl-4,5-dihydro-1H-pyrazole-1-carboximidamido)-3-hydroxybutanamide | |
| 2e (2S,3S,4'R) | (2S,3S)-2-((R)-3-(4-chlorophenyl)-N'-((4-chlorophenyl)sulfonyl)-4-phenyl-4,5-dihydro-1H-pyrazole-1-carboximidamido)-3-hydroxybutanamide | |
| 2f (2R,3S,4'S) | (2R,3S)-2-((S)-3-(4-chlorophenyl)-N'-((4-chlorophenyl)sulfonyl)-4-phenyl-4,5-dihydro-1H-pyrazole-1-carboximidamido)-3-hydroxybutanamide | |
| 2g (2R,3S,4'R) | (2R,3S)-2-((R)-3-(4-chlorophenyl)-N'-((4-chlorophenyl)sulfonyl)-4-phenyl-4,5-dihydro-1H-pyrazole-1-carboximidamido)-3-hydroxybutanamide | |
| 3 (2S,4'S) | | ++++ |
| 3a (2S,4'R) | | ++ |

TABLE 1-continued

| Ex. # | Structure | CB1 IC$_{50}$ |
|---|---|---|
| 3b (2R,4'S) | 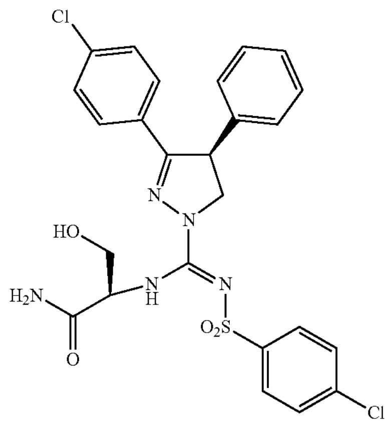 [SMILES: NC(=O)[C@@H](CO)N/C(=N\S(=O)(=O)c1ccc(Cl)cc1)N1C[C@H](c2ccccc2)C(c2ccc(Cl)cc2)=N1] | |
| 3c (2R,4'R) | 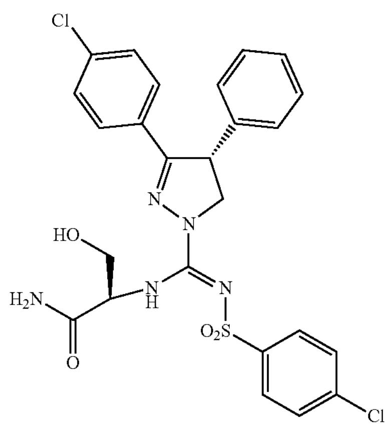 [SMILES: NC(=O)[C@@H](CO)N/C(=N\S(=O)(=O)c1ccc(Cl)cc1)N1C[C@@H](c2ccccc2)C(c2ccc(Cl)cc2)=N1] | |
| 4 (2S,4'S) | 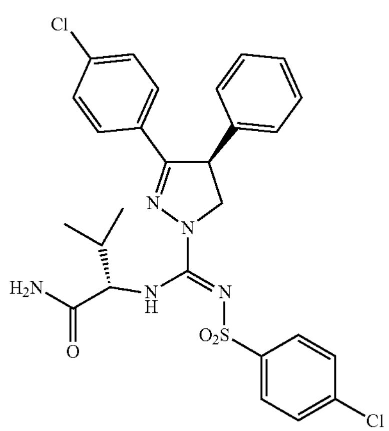 [SMILES: CC(C)[C@H](N/C(=N\S(=O)(=O)c1ccc(Cl)cc1)N1C[C@H](c2ccccc2)C(c2ccc(Cl)cc2)=N1)C(N)=O] | ++++ |
| 4a (2S,4'R) | 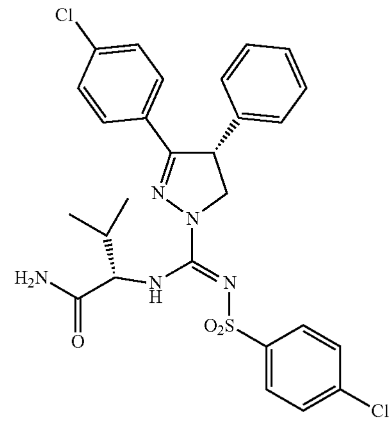 [SMILES: CC(C)[C@H](N/C(=N\S(=O)(=O)c1ccc(Cl)cc1)N1C[C@@H](c2ccccc2)C(c2ccc(Cl)cc2)=N1)C(N)=O] | + |
| 4b (2R,4'S) | 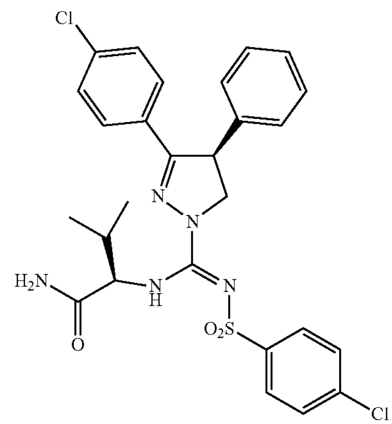 [SMILES: CC(C)[C@@H](N/C(=N\S(=O)(=O)c1ccc(Cl)cc1)N1C[C@H](c2ccccc2)C(c2ccc(Cl)cc2)=N1)C(N)=O] | |
| 4c (2R,4'R) | 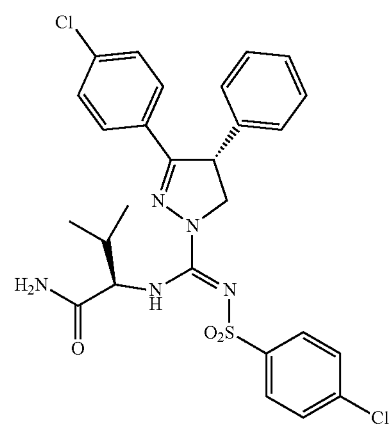 [SMILES: CC(C)[C@@H](N/C(=N\S(=O)(=O)c1ccc(Cl)cc1)N1C[C@@H](c2ccccc2)C(c2ccc(Cl)cc2)=N1)C(N)=O] | |

Numerous modifications and variations of the present invention are possible in light of the above teachings. It is therefore to be understood that within the scope of the appended claims, the invention may be practiced otherwise that as specifically described herein.

What is claimed is:

1. A method of treating a disease comprising administering to a mammal in need thereof a therapeutically effective amount of a compound selected from any one of compounds 1, 2, 3, and 4:

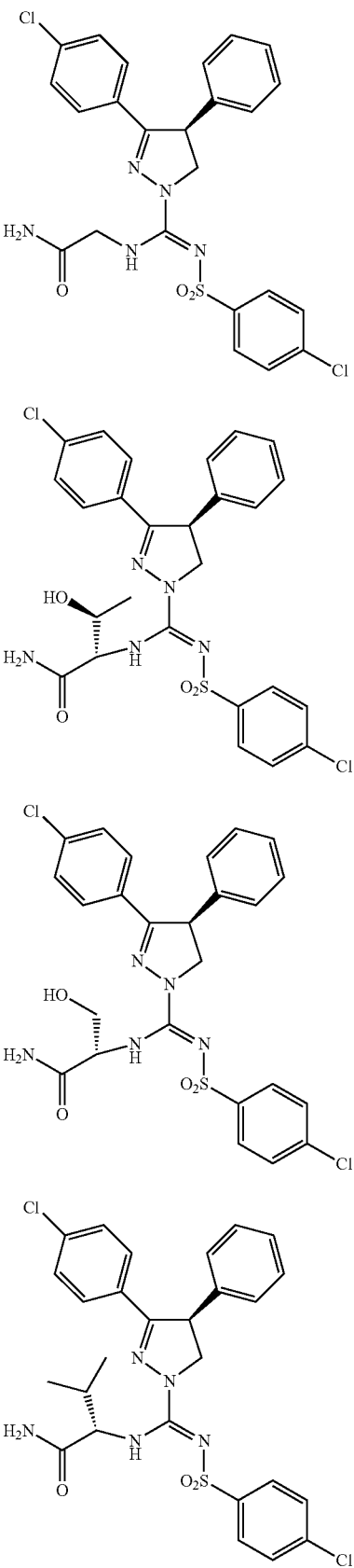

or a pharmaceutically acceptable salt thereof, wherein the disease is obesity or a co-morbidity of obesity.

2. The method of claim 1, wherein the compound is compound 1 or a pharmaceutically acceptable salt thereof, wherein the stereomeric purity is at least 60%.

3. The method of claim 2, wherein the stereomeric purity is at least 95%.

4. The method of claim 1, wherein the compound is compound 2 or a pharmaceutically acceptable salt thereof, wherein the stereomeric purity is at least 60%.

5. The method of claim 4, wherein the stereomeric purity is at least 95%.

6. The method of claim 1, wherein the compound is compound 3 or a pharmaceutically acceptable salt thereof, wherein the stereomeric purity is at least 60%.

7. The method of claim 6, wherein the stereomeric purity is at least 95%.

8. The method of claim 1, wherein the compound is compound 4 or a pharmaceutically acceptable salt thereof, wherein the stereomeric purity is at least 60%.

9. The method of claim 8, wherein the stereomeric purity is at least 95%.

10. The method of claim 1, wherein the co-morbidity of obesity is selected from diabetes, dyslipidemias, Metabolic Syndrome, dementia, cardiovascular disease, hepatic disease, hypertension, gallbladder disease, gastrointestinal disorders, menstrual irregularities, degenerative arthritis, venous stasis ulcers, pulmonary hypoventilation syndrome, sleep apnea, snoring, coronary artery disease, arterial sclerotic disease, pseudotumor cerebri, accident proneness, increased risks with surgeries, osteoarthritis, high cholesterol, and increased incidence of malignancies of the ovaries, cervix, uterus, breasts, prostrate, or gallbladder.

11. The method of claim 10, wherein the diabetes is Type 2 diabetes.

12. The method of claim 10, wherein the dyslipidemia is selected from low levels of high-density lipoprotein, high levels of low-density lipoprotein, and high levels of triglycerides, or any combination thereof.

13. The method of claim 10, wherein the cardiovascular disorder is selected from atherosclerosis, hypertension, stroke, and heart attack.

14. A method of treating a disease, comprising administering to a mammal in need thereof a therapeutically effective amount of
 a. a first therapeutic agent that is a compound of claim 1 or a pharmaceutically acceptable salt thereof, and
 b. a second therapeutic agent;
 wherein the disease is obesity or a co-morbidity of obesity, and the second therapeutic agent is useful for treating the disease.

15. The method of claim 14, wherein the compound is compound 4 or a pharmaceutically acceptable salt thereof, wherein the stereomeric purity is at least 60%.

16. The method of claim 15, wherein the stereomeric purity is at least 95%.

17. The method of claim 14, wherein the co-morbidity of obesity is selected from diabetes, dyslipidemias, Metabolic Syndrome, dementia, cardiovascular disease, hepatic disease, hypertension, gallbladder disease, gastrointestinal disorders, menstrual irregularities, degenerative arthritis, venous stasis ulcers, pulmonary hypoventilation syndrome, sleep apnea, snoring, coronary artery disease, arterial sclerotic disease, pseudotumor cerebri, accident proneness, increased risks with surgeries, osteoarthritis, high cholesterol, and increased incidence of malignancies of the ovaries, cervix, uterus, breasts, prostrate, or gallbladder.

18. The method of claim 17, wherein the diabetes is Type 2 diabetes.

19. The method of claim 17, wherein the dyslipidemia is selected from low levels of high-density lipoprotein, high levels of low-density lipoprotein, and high levels of triglycerides, or any combination thereof.

20. The method of claim 17, wherein the cardiovascular disorder is selected from atherosclerosis, hypertension, stroke, and heart attack.

\* \* \* \* \*